United States Patent  (10) Patent No.: US 8,340,768 B2
Seim et al.  (45) Date of Patent: Dec. 25, 2012

(54) SENSING THRESHOLD CONTROL TO LIMIT AMPLITUDE TRACKING

(75) Inventors: Gary T. Seim, Minneapolis, MN (US); Ron A. Balczewski, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 917 days.

(21) Appl. No.: 12/330,857

(22) Filed: Dec. 9, 2008

(65) Prior Publication Data

US 2009/0157128 A1  Jun. 18, 2009

Related U.S. Application Data

(60) Provisional application No. 61/007,456, filed on Dec. 12, 2007.

(51) Int. Cl.
*A61N 1/37* (2006.01)
(52) U.S. Cl. .............................. 607/28; 607/13; 600/509
(58) Field of Classification Search .................. 607/4, 5, 607/9, 18, 28, 31; 600/509
See application file for complete search history.

(56) References Cited

U.S. PATENT DOCUMENTS

| | | | |
|---|---|---|---|
| 5,458,621 A | 10/1995 | White et al. | |
| 5,620,466 A | 4/1997 | Haefner et al. | |
| 5,658,317 A | 8/1997 | Haefner et al. | |
| 5,755,738 A | 5/1998 | Kim et al. | |
| 6,169,918 B1 | 1/2001 | Haefner et al. | |
| 6,208,888 B1 | 3/2001 | Yonce | |
| 6,282,446 B1 | 8/2001 | Eberle et al. | |
| 6,304,778 B1 | 10/2001 | Gilkerson et al. | |
| 6,438,406 B2 | 8/2002 | Yonce | |
| 6,473,649 B1 * | 10/2002 | Gryzwa et al. | 607/28 |
| 6,510,339 B2 | 1/2003 | Kovtun et al. | |
| 6,584,350 B2 | 6/2003 | Kim et al. | |
| 6,591,136 B2 | 7/2003 | Eberle et al. | |
| 6,643,540 B2 | 11/2003 | Yonce | |
| 6,687,539 B2 | 2/2004 | Gilkerson et al. | |
| 6,778,855 B2 | 8/2004 | Eberle et al. | |
| 6,834,205 B2 | 12/2004 | Eberle et al. | |
| 6,853,860 B2 | 2/2005 | Eberle et al. | |
| 6,873,875 B1 | 3/2005 | Gilkerson et al. | |
| 6,925,325 B2 | 8/2005 | Yonce | |
| 6,928,323 B2 | 8/2005 | Kim et al. | |
| 6,950,694 B2 | 9/2005 | Yonce | |
| 7,200,436 B2 | 4/2007 | Gilkerson et al. | |
| 2003/0158586 A1 | 8/2003 | Mouchawar et al. | |
| 2004/0230232 A1 | 11/2004 | Gilkerson et al. | |
| 2005/0004613 A1 * | 1/2005 | Zhang et al. | 607/28 |
| 2006/0085038 A1 | 4/2006 | Linder et al. | |
| 2006/0247707 A1 | 11/2006 | Meyer et al. | |
| 2006/0271120 A1 | 11/2006 | Ternes | |
| 2007/0135851 A1 | 6/2007 | Gilkerson et al. | |

* cited by examiner

*Primary Examiner* — Carl H. Layno
*Assistant Examiner* — Jon-Eric C. Morales
(74) *Attorney, Agent, or Firm* — Schwegman Lundberg & Woessner, P.A.

(57) ABSTRACT

A depolarization sensing threshold can be determined using an amplitude-limited portion of a cardiac signal received using an implantable medical device. One or more cardiac depolarizations can be detected using the cardiac signal and the depolarization sensing threshold.

21 Claims, 5 Drawing Sheets

SENSING THRESHOLD CONTROL TO LIMIT AMPLITUDE TRACKING

CLAIM OF PRIORITY

This patent application claims the benefit of priority, under 35 U.S.C. Section 119(e), to Seim et al., U.S. Provisional Patent Application Ser. No. 61/007,456, entitled "AUTOMATIC GAIN CONTROL TO LIMIT AMPLITUDE TRACKING," filed on Dec. 12, 2007, incorporated herein by reference in its entirety.

BACKGROUND

Implantable medical devices (IMDs) can include cardiac rhythm management (CRM) devices such as pacemakers, cardioverter/defibrillators, and cardioverter/defibrillators with pacing capability, or one or more other types of devices. A CRM device can detect one or more dangerous cardiac arrhythmia conditions in the heart, such as a bradycardia, a tachycardia, a fibrillation, or one or more other arrhythmias such as by measuring the time interval between one or more consecutive cardiac depolarizations.

Overview

This overview is intended to provide an overview of subject matter of the present patent application. It is not intended to provide an exclusive or exhaustive explanation of the invention. The detailed description is included to provide further information about the present patent application.

In an example, a depolarization sensing threshold can be determined using an amplitude-limited portion of a cardiac signal received using an implantable medical device. In an example, one or more cardiac depolarizations can be detected using the cardiac signal and the depolarization sensing threshold.

In Example 1, an implantable medical device can include an input configured to receive a cardiac signal, a first comparator configured to receive the cardiac signal from the input and to provide an amplitude-limited portion of the cardiac signal, a depolarization sensing threshold generation circuit configured to provide a depolarization sensing threshold using the amplitude-limited portion of the cardiac signal, and a depolarization detection circuit configured to detect a cardiac depolarization using the cardiac signal and the depolarization sensing threshold.

In Example 2, the input of Example 1 optionally includes an analog-to-digital (A/D) converter configured to convert an analog signal representative of cardiac activity into digital data, and the cardiac signal optionally includes the digital data.

In Example 3, the depolarization sensing threshold generation circuit of any one or more of Examples 1-2 is optionally configured to provide the depolarization sensing threshold at least in part using integer math.

In Example 4, the A/D converter of any one or more of Examples 1-3 is optionally configured to convert the analog signal into digital data using a single gain range without requiring clipping of the analog signal when the analog signal optionally includes both a depolarization of a typical amplitude and a depolarization of amplitude substantially greater than the depolarization of the typical amplitude.

In Example 5, the depolarization sensing threshold generation circuit of any one or more of Examples 1-4 optionally includes a peak detector configured to receive the amplitude-limited portion of the cardiac signal, to detect at least one of a peak or a minimum of the amplitude-limited portion of the cardiac signal, and to provide at least one of the detected peak or the detected minimum of the amplitude-limited portion of the cardiac signal to the depolarization sensing threshold generation circuit, and the depolarization sensing threshold is optionally substantially equal to at least one of the detected peak or the detected minimum of the amplitude-limited portion of the cardiac signal.

In Example 6, the depolarization detection circuit of any one or more of Examples 1-5 optionally includes a second comparator configured to compare the cardiac signal with the depolarization sensing threshold and to provide an event signal when the cardiac signal exceeds the depolarization sensing threshold.

In Example 7, the depolarization sensing threshold generation circuit of any one or more of Examples 1-6 is optionally configured to provide the depolarization sensing threshold to the detection circuit for a current cardiac cycle in response to the event signal.

In Example 8, the depolarization sensing threshold generation circuit of any one or more of Examples 1-7 is optionally configured to vary the depolarization sensing threshold level as a function of time during a particular cardiac cycle.

In Example 9, the depolarization threshold generation circuit of any one or more of Examples 1-8 is optionally configured to determine a depolarization sensing threshold peak value for a current cardiac cycle using a depolarization sensing threshold peak value from a previous cardiac cycle and the amplitude-limited portion of the cardiac signal.

In Example 10, the depolarization sensing threshold generation circuit of any one or more of Examples 1-9 is optionally configured to decrease the depolarization sensing threshold as a function of time, during the particular cardiac cycle, in one or more discrete steps following a piecewise linear approximation of a geometric progression, and the one or more discrete steps optionally include a first depolarization sensing threshold provided at the beginning of the particular cardiac cycle, and a second depolarization sensing threshold equal to approximately 75% of the first depolarization sensing threshold.

In Example 11, a method includes receiving a cardiac signal using an implantable medical device, limiting an amplitude of the received cardiac signal to provide an amplitude-limited portion of the cardiac signal, determining a depolarization sensing threshold using the amplitude-limited portion of the cardiac signal, detecting a cardiac depolarization using the cardiac signal and the depolarization sensing threshold.

In Example 12, the method of Example 11 optionally includes detecting a peak of a received cardiac signal during a particular cardiac cycle, and the limiting the amplitude optionally includes limiting the amplitude of the received cardiac signal to a percentage relative to the peak, the percentage specified using at least one programmable limit, to provide the amplitude-limited portion of the cardiac signal.

In Example 13, the determining the depolarization sensing threshold of any one or more of Examples 11-12 optionally includes detecting at least one of a peak or a minimum of the amplitude-limited portion of the cardiac signal, and optionally providing, in response to the detecting, a depolarization sensing threshold substantially equal to at least one of the detected peak or the detected minimum of the amplitude-limited portion of the cardiac signal.

In Example 14, the detecting the cardiac depolarization of any one or more of Examples 11-13 optionally includes comparing the received cardiac signal with the depolarization sensing threshold, and optionally providing an event signal when the received cardiac signal exceeds the depolarization sensing threshold.

In Example 15, the determining the depolarization sensing threshold of any one or more of Examples 11-14 optionally includes providing a depolarization sensing threshold substantially equal to at least one of the peak or the minimum of the amplitude-limited portion of the cardiac signal in response to the event signal.

In Example 16, the determining the depolarization sensing threshold of any one or more of Examples 11-15 optionally includes varying the depolarization sensing threshold as a function of time during a particular cardiac cycle.

In Example 17, the determining the depolarization sensing threshold of any one or more of Examples 11-16 optionally includes determining a depolarization sensing threshold peak for a current cardiac cycle using a depolarization sensing threshold peak value from a previous cardiac cycle and the amplitude-limited portion of the cardiac signal.

In Example 18, the determining the depolarization sensing threshold of any one or more of Examples 11-17 optionally includes decreasing the depolarization sensing threshold in one or more discrete steps following a piecewise linear approximation of a geometric progression, and the one or more discrete steps optionally include using a first depolarization sensing threshold, provided at the beginning of the particular cardiac cycle, and using a second depolarization sensing threshold equal to approximately 75% of the first depolarization sensing threshold at a later time during the particular cardiac cycle.

In Example 19, the receiving the signal of any one or more of Examples 11-18 optionally includes receiving an analog signal representative of the cardiac activity and optionally converting the analog signal into a digital signal using an analog-to-digital (A/D) converter.

In Example 20, the receiving the signal includes of any one or more of Examples 11-19 optionally includes receiving an analog signal representative of the cardiac activity, and optionally converting the analog signal into a digital signal using an analog-to-digital (A/D) converter having a single gain range without requiring clipping of the analog signal when the analog signal comprises both a depolarization of a typical amplitude and a depolarization of amplitude substantially greater than the depolarization of the typical amplitude.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
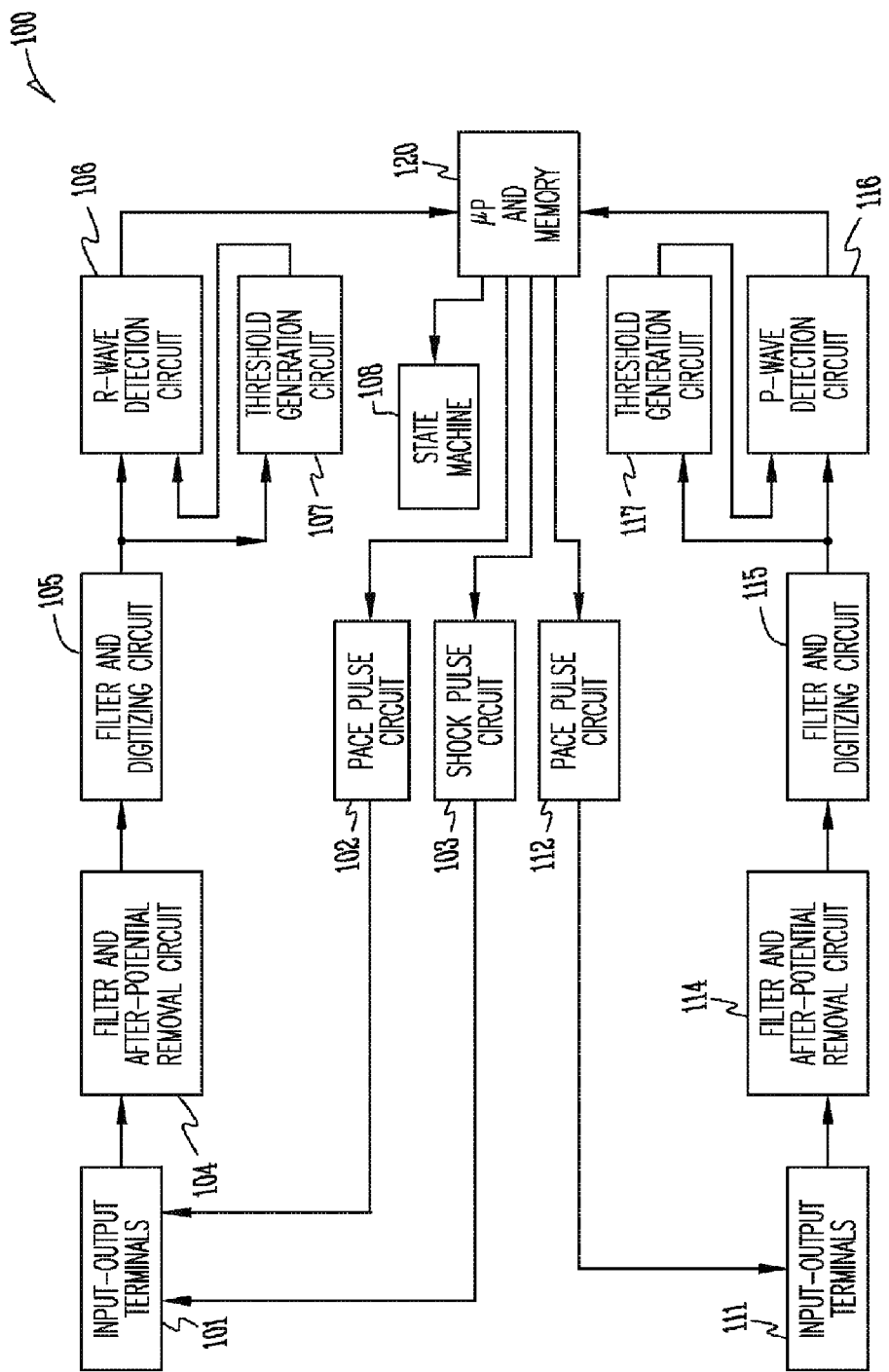
FIG. 1 illustrates generally a cardiac rhythm management (CRM) device, according to various embodiments.

The present application incorporates U.S. Pat. No. 5,658,317, entitled "THRESHOLD TEMPLATING FOR DIGITAL AGC," and assigned to Cardiac Pacemakers, Inc., by reference herein in its entirety.

Cardiac rhythm management devices can receive a sensed cardiac signal comprising electrical activity of the heart and detect cardiac depolarizations in the electrical activity when an amplitude of the electrical activity exceeds one or more predetermined amplitude levels or "sensing thresholds." A depolarization sensing threshold can be fixed, or can be varied over time. The present inventors have recognized that a fixed depolarization sensing threshold can be inappropriate for detecting certain arrhythmias, such as polymorphic tachycardia, fibrillation, or premature ventricular contractions (PVCs) wherein extreme variations in the amplitude of the electrical activity can occur during the arrhythmia. For example, an amplitude of electrical activity associated with an arrhythmia such as polymorphic tachycardia, fibrillation, or a premature ventricular contraction can be substantially greater than a depolarization of typical amplitude. The problem of tracking variations in the amplitude of the electrical activity can be further complicated when the cardiac rhythm management device delivers pace pulses to the heart, which can cause evoked responses or one or more other electrical signals which are substantially higher than a typical amplitude associated with one or more intrinsic depolarizations.

The present application discloses, among other things, systems and methods to limit amplitude tracking for variable depolarization sensing threshold control. Certain embodiments of the present subject matter can include an A/D converter, such as with a single gain range, configured to cover the entire range of potentials representative of a cardiac signal representative of cardiac electrical activity (e.g., on the order of less than about 100 microvolts to on the order of about 25 millivolts or greater). Certain embodiments can include a 12-bit A/D converter. In an embodiment, one bit can be a sign bit, and the remaining eleven bits can be used as incremental values such as when converting one or more analog signals derived from the cardiac signal to one or more digital signals. In certain embodiments, the use of the single gain range to convert analog to digital can provide a digital signal more closely reflecting the actual cardiac signal waveform, showing amplitude or timing information with less distortion compared to the use of more than one gain range (e.g., without requiring clipping, or without inducing one or more other nonlinearities associated with using more than one gain range). Generally, in certain embodiments, the depolarization sensing threshold can be reactive to the peak value of the detected cardiac signal, a rolling average of previous cycles, or one or more other features or central tendencies of the detected cardiac signal. The present subject matter can be used to limit the change in a depolarization sensing threshold while still providing a depolarization sensing threshold reactive to a beat-to-beat variation, or one or more other variations in the detected cardiac signal. This can prevent the depolarization sensing threshold from being overly sensitive to abnormally high or low peaks in the detected cardiac signal, such as an abnormally high peak or an abnormally high amplitude associated with a premature ventricular contraction (PVC).

FIG. 1 illustrates generally an example of a cardiac rhythm management (CRM) device 100. The illustrated embodiment can be discussed with reference to an atrial lead to stimulate an atrial region and a ventricular lead to stimulate a ventricular region. However, the present application need not be limited to a particular number of leads nor limited to the stimulation of particular cardiac regions. For example, one or more electrocardiograms or other signals representative of cardiac activity can be sensed and limited according to the present subject matter such as using a subcutaneous implantable medical device, or one or more other medical devices.

The CRM device 100 can be operated as a pulse generator device portion of a cardiac rhythm management system, and the system can also include one or more leads or electrodes disposed in, for example, the ventricular chamber of a heart to sense electrical activity representative of an R-wave portion of the PQRST complex indicating a depolarization in the ventricle as shown similarly on, for example, a skin surface electrocardiogram (EGM). The CRM device 100 can include one or more input/output terminals 101 which can be connectable to the one or more leads to receive, for example, an analog signal representative of the ventricular electrical activity of the heart sensed by the ventricular leads. A pace pulse circuit 102 can provide electrostimulation such as one or more of bradycardia or antitachycardia pacing pulses to the input/output terminals. In an embodiment, one or more electrostimulation pulses can be provided to the ventricular chamber of the heart via the ventricular leads to stimulate excitable myocardial tissue to treat arrhythmia conditions such as bradycardia, tachycardia, congestive heart failure, or one or more other heart-related diseases. A shock pulse circuit 103 can provide one or more shock pulses to input/output terminals, for example, to be provided to the ventricular chamber of the heart via the ventricular leads to shock excitable myocardial tissue to treat (e.g., defibrillate) tachyarrhythmia conditions. The tachyarrhythmia conditions can include ventricular fibrillation, or ventricular tachycardia, or one or more other conditions.

A filter and after-potential removal circuit 104 can be used to filter, for example, the ventricular electrical activity received by the input/output terminals 101, or the pacing pulses provided from the pacing pulse circuit 102. In addition, the filter and after-potential removal circuit 104 can remove after-potential created by, for example, a pacing pulse from the pacing pulse circuit 102 or a shock pulse delivered by the shock pulse circuit 103.

A filter and digitizing circuit 105 can be configured to transform the cardiac signal in one or more ways, such as by converting, processing, modifying or amplifying the filtered ventricular electrical activity provided from the filter and after-potential removal circuit 104. The filter and digitizing circuit 105 can include circuitry (e.g., an A/D converter or one or more other circuits), such as for digitizing the filtered ventricular electrical activity. An R-wave depolarization detection circuit 106 can be coupled to the filter and digitizing circuit 105, such as to detect depolarizations in the amplified ventricular electrical activity representative of R-wave depolarizations when the amplified ventricular electrical activity exceeds a selected amplified level known as a depolarization "sensitivity threshold" or a depolarization "sensing threshold," and one or more refractories are inactive. A depolarization sensing threshold generation circuit, such as threshold generation circuit 107 can automatically select or adjust the depolarization sensing threshold. The R-wave depolarization detection circuit can provide an R-wave depolarization signal indicative of the R-wave depolarizations to, for example, a microprocessor or memory (e.g., microprocessor and memory 120).

The CRM device 100 can also include one or more leads or electrodes disposed in the atrial chamber of the heart, such as to sense electrical activity representative of a P-wave portion of the PQRST complex of a surface EGM indicating depolarizations in the atrium. The CRM device 100 can include one or more input/output terminals 111 connectable to the atrial leads, such as to receive the atrial electrical activity of the heart sensed by the atrial leads. A pace pulse circuit 112 can provide low voltage electrostimulation such as bradycardia pacing pulses to the input/output terminals 111, the electrostimulation to be provided to the atrial chamber of the heart via the atrial leads such as to stimulate excitable myocardial tissue to treat arrhythmia conditions such as bradycardia, atrial tachycardia, or one or more other conditions. A filter and after-potential removal circuit 114 can operate similarly to the filter and after-potential removal circuit 104, such as to filter the atrial electrical activity received by the input/output terminals 111 and the pacing pulses provided from the pacing pulse circuit 112. In addition, the filter and after-potential removal circuit 114 can remove the after-potential created by a pacing pulse from the pacing pulse circuit 112.

A filter and digitizing circuit 115 can be configured to transform the cardiac signal in one or more ways, such as by converting, processing, modifying or amplifying the filtered atrial electrical activity provided from the filter and after-potential removal circuit 114. The filter and digitizing circuit 115 can include circuitry (e.g. A/D converter, or one or more other circuits) for digitizing the filtered atrial electrical activity. A P-wave depolarization detection circuit can be coupled to the filter and digitizing circuit such as to detect depolarizations in the amplified atrial electrical activity representative of P-wave depolarizations when the amplified atrial electrical activity exceeds a selected amplified level known as a depolarization "sensitivity threshold" or a depolarization "sensing threshold" and one or more refractories are inactive. A depolarization sensing threshold generation circuit, such as threshold generation circuit 117 can automatically select or adjust the depolarization sensing threshold. The P-wave depolarization detection circuit can provide a P-wave depolarization signal, indicative of one or more P-wave depolarizations, such as to the microprocessor and memory 120 or one or more other portions, parts or components of CRM device 100. In certain embodiments, the microprocessor and memory 120 can then alter an operational mode of the CRM device 100 in response one or more sensed depolarizations such as to inhibit therapy delivery for one or more cardiac cycles (e.g., to suppress a pace pulse delivery when an intrinsic event is detected), or to initiate therapy delivery (e.g., to deliver a triggered pace pulse when an intrinsic event is detected), or to apply one or more detection methods to differentiate between one or more arrhythmias (e.g., to determine whether a tachycardia is occurring).

The microprocessor and memory 120 can analyze the detected P-waves, such as indicated in the P-wave depolarization signal from P-wave depolarization detection circuit, along with the R-wave depolarization signal provided from R-wave depolarization detection circuit, for the detection of one or more arrhythmia conditions using one or more arrhythmia detection algorithms. For example, the microprocessor and memory 120 can be used to analyze the rate, regularity, or onset of variations in the rate of the reoccurrence of one or more detected P-waves or R-waves, the morphology of one or more detected P-waves or R-waves, the direction of propagation of the depolarization represented by one or more detected P-waves or R-waves in the heart, or one or more other signals or parameters derived from information obtained from one or more physiologic sensors. In addition, the microprocessor and memory 120 can store depolarization data and, for example, can analyze one or more detected P-waves or R-waves to control one or more of a pace pulse circuit or a shock pulse circuit for delivery of pace pulses or shock pulses to a tissue site, such as the ventricle. In an example, the microprocessor and memory 120 can use one or more detected P-waves to control a pace pulse circuit for proper delivery of one or more pace pulses to the atrium. In an example, the microprocessor and memory 120 can include or control one or more state machines 108, such as to place one or more circuits of the CRM device 100 in one or more logical states based on various conditions such as when a pace pulse or shock pulse occurs or on operating conditions of the CRM device 100 such as bradycardia pacing, anti-tachyarrhythmia pacing, tachyarrhythmia sensing, normal sinus sensing, or one or more other operating conditions.

Figure 2:
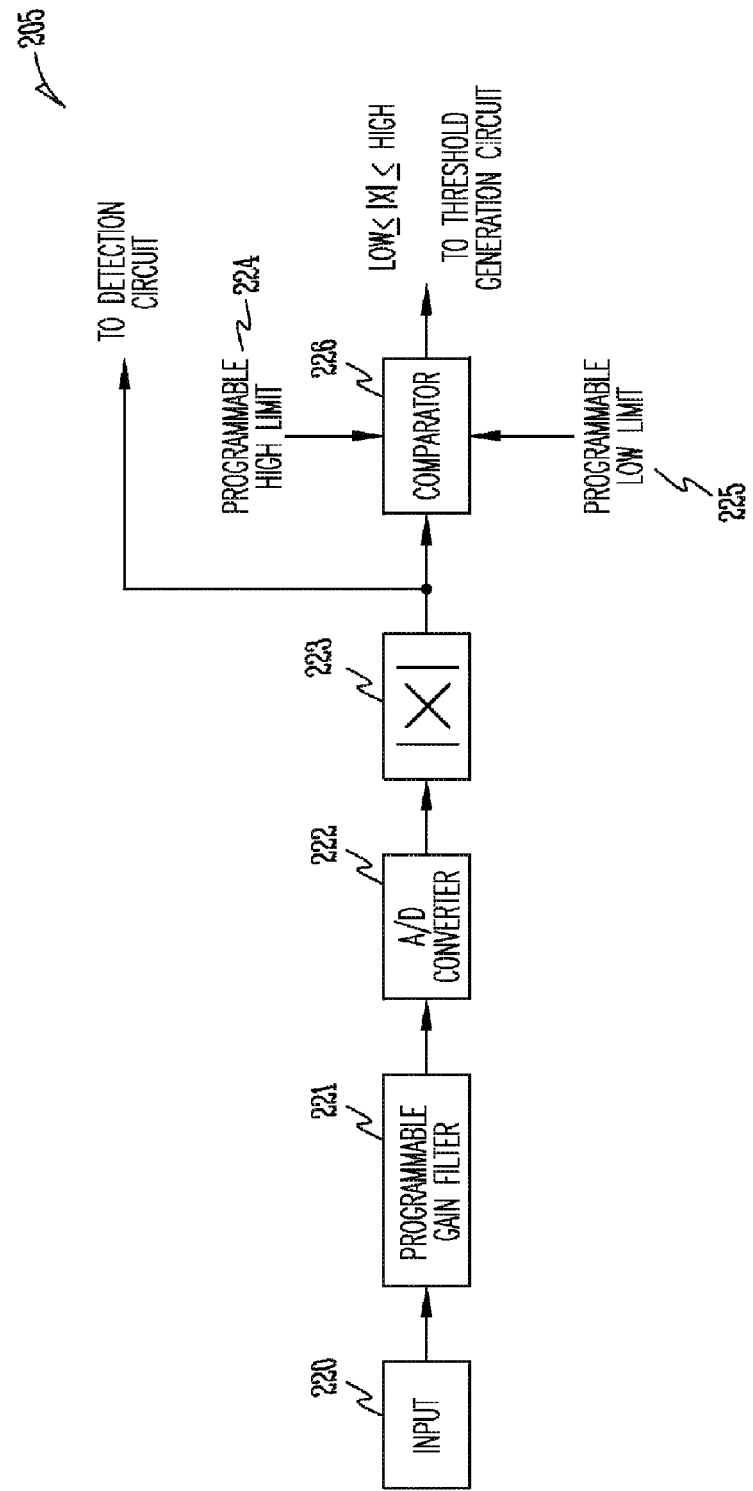
FIG. 2 illustrates generally a logical block diagram representative of a filter and digitizing circuit, according to various embodiments.

FIG. 2 illustrates generally a logical block diagram representative of a filter and digitizing circuit 205, such as the filter and digitizing circuit 105 or the filter and digitizing circuit 115 in the example of FIG. 1. A programmable gain filter 221 filters the electrical activity provided a filter and after-potential removal circuit, such as circuit 104 or circuit 114 as shown in the example of FIG. 1. An analog to digital (A/D) converter 222 can receive filtered or amplified electrical activity from the programmable gain filter 221 and can convert an analog signal representative of cardiac electrical activity (e.g., a signal containing information derived from one or more physiologic sensors such as an electrocardiogram signal, or one or more other analog signals) into digital data. According to various embodiments, the A/D converter 222 can be a 12-bit converter capable of processing the entire cardiac signal range (e.g. on the order of about 100 microvolts or less to on the order of about 25 millivolts or greater) without changing gains (e.g., without requiring using more than one gain range on an amplifier or filter such as the programmable gain filter 221 or one or more other amplifiers, filters, analog-to-digital converters, or other circuits or modules).

The A/D converter 221 can provide the stored digital data to an absolute value circuit 223, which can provide the absolute value of the amplitude of the digital data to, for example, the threshold generation circuit 107 or the threshold generation circuit 117, such as shown in the example of FIG. 1. The threshold generation circuit 107 or the threshold generation circuit 117 can provide a rapidly responding variable depolarization sensing threshold to the depolarization detection circuit (e.g., varying with respect to time during a particular cardiac cycle or across one or more cardiac cycles), such as for sensing of R-wave or P-wave depolarizations representative of cardiac events.

In an example, the threshold generation circuit 107 or the threshold generation circuit 117, such as shown in the example of FIG. 1, can be substantially similar to or the same as a template generation circuit such as shown and discussed in the context of FIG. 7 of U.S. Pat. No. 5,658,317, entitled "THRESHOLD TEMPLATING FOR DIGITAL AGC," previously incorporated by reference, and can provide a time varying depolarization sensing threshold, such as to detect one or more depolarization events. In certain examples, the depolarization sensing threshold can be based on a rolling average of the past "m" beats, or one or more other parameters. The depolarization detection circuit (such as R-wave depolarization detection circuit 106 or a P-wave depolarization detection circuit 116 as shown in the example of FIG. 1, or one or more other detection circuits) can provide an event signal indicating one or more R-wave or P-wave depolarizations representative of cardiac events when the value of the incoming digital cardiac data is greater than the depolarization sensing threshold level provided that one or more refractory or blanking windows are inactive. The threshold generation circuit, such as threshold generation circuit 107 or the threshold generation circuit 117 can include circuitry for selecting and adjusting the variable depolarization sensing threshold to a level proportional to the amplitude of the digital cardiac data, such as by using one or more parameters derived from the digital cardiac data (e.g., an instantaneous peak value, a peak value as measured during an interval, an average value over one or more cardiac cycles, or one or more other parameters). In an example, the threshold generation circuit 107 or the threshold generation circuit 117 can respond rapidly to change the depolarization sensing threshold to the peak value of the digital cardiac data, such as during an interval defined by a cardiac cycle (e.g., an interval between two successive R-waves or two successive P-waves, or one or more other intervals). In an example, the variable depolarization sensing threshold can be held at or near the peak value for a selected period of time, such as at the beginning of a cardiac cycle, after which the variable depolarization sensing threshold can be decreased to a specified percentage of the peak value. The variable depolarization sensing threshold can then be further decreased in discrete steps until the variable depolarization sensing threshold is at a low limit value. In an example, the threshold generation circuit 107 or the threshold generation circuit 117 can use integer math to provide one or more threshold templates (e.g., a progression, pattern or sequence of one or more variable depolarization sensing threshold values to be provided) following a piecewise linear approximation of a geometric progression such as an exponential decay curve, or one or more other decay curves, with minimal error between piecewise steps.

In an example, the A/D converter 222 can process one or more cardiac signals (e.g., one or more intrinsic depolarizations, electrostimulations, PVCs or one or more other events) without clipping, such as by using a single gain range. The present inventors have recognized that at least one programmable limit (e.g. a programmable high limit 224 or programmable low limit 225, or one or more other limits) can be used to provide an amplitude-limited portion of the cardiac signal (e.g., a signal including an amplitude-limited by one or more thresholds) to the threshold generation circuit for use in providing the depolarization sensing threshold, or to limit a change in the depolarization sensing threshold. In the example shown in FIG. 2, a comparator 226 can be coupled to the absolute value circuit 223 and can provide an amplitude-limited portion of the cardiac signal to the threshold generation circuit, such as the threshold generation circuit 107 or the threshold generation circuit 117 shown in the example of FIG. 1, or one or more other circuits.

In an illustrative example, a programmable high limit 224 can be an amplitude value, or can be a proportion, such as specified by a percentage. In this example, a proportion such as approximately 150% can be specified, and can limit the change used in the depolarization sensing threshold determination to 150% of the detected peak amplitude of one or more of the previous cardiac events (e.g., an R-wave, a P-wave, a PVC, or one or more other events occurring during a previous cardiac cycle). The present inventors have recognized that the threshold generation circuit need not overreact to a premature ventricular contraction (PVC), for example, or one or more other abnormally high amplitude sensed signals when the change used in the depolarization sensing threshold determination can be limited. In the absence of the programmable high limit and the limit to the change used in the depolarization sensing threshold determination, a CRM device 100, such as shown in the example of FIG. 1, can under-sense one or more cardiac events (e.g., fail to achieve a depolarization sensing threshold crossing) after detecting and tracking a PVC or one or more other cardiac signals having an amplitude substantially larger than a typical cardiac signal, since one or more subsequent threshold steps can be abnormally elevated in comparison to a typical depolarization sensing threshold, and in relation to the typical depolarization amplitude.

In an illustrative example, a low limit can be approximately 50%, and can limit the change in the depolarization sensing threshold determination to 50% of the detected peak of the previous pulse. In the absence of the programmable low limit and limit to the change used in the depolarization sensing threshold determination, a CRM device 100, such as shown in the example of FIG. 1, can over-sense (e.g., erroneously detect a noise signal or one or more other non-cardiac signals as a cardiac event) since one or more subsequent threshold steps can be abnormally lowered. In certain examples, other values can be used for the high limit and for the low limit. Thus, in certain examples, using the programmable high limit or the programmable low limit, the beat-to-beat variation of the peak amplitude presented to the threshold generation circuit to provide the depolarization sensing threshold can be limited to avoid undesired tracking of abnormal events. If the actual peak amplitude of a cardiac signal is higher than the high limit, the high limit can be passed as the peak value of the cardiac signal for use by the threshold generation circuit. If the sensed peak of the pulse is lower than the low limit, the low limit can be passed as the peak for use by the threshold generation circuit 107 or the threshold generation circuit 117, or one or more other circuits.

Certain embodiments can adjust the depolarization sensing threshold based on a previous depolarization pulse (e.g., a peak amplitude of the most recent cardiac event as derived from a cardiac signal, or one or more other features of a previous pulse). Certain embodiments can adjust the depolarization sensing threshold based on a rolling average of a plurality of features of one or more preceding pulses. Certain embodiments can use an exponential average of one or more features of the previous pulses (e.g. $\frac{1}{5}$ of the peak amplitude of the last beat +$\frac{4}{5}$ of the peak amplitude of one or more other preceding beats).

Figure 3:
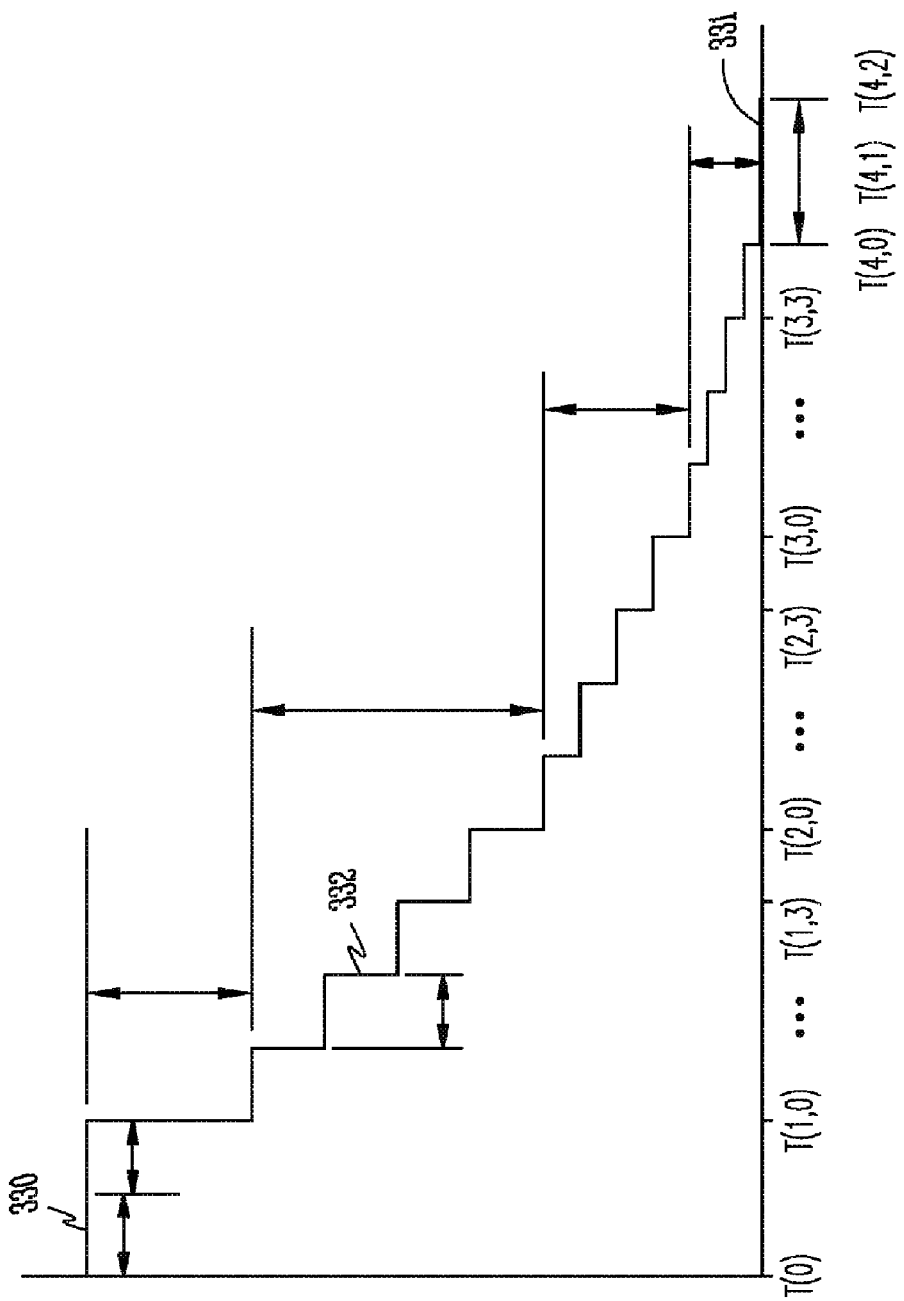
FIG. 3 illustrates generally a timing diagram showing a variable sensing threshold generated by a depolarization sensing threshold generation circuit and provided to a depolarization detection circuit.

FIG. 3 illustrates generally a timing diagram showing a variable depolarization sensing threshold, such as varying as a function of time, generated by a threshold generation circuit, such as the threshold generation circuit 107 or the threshold generation circuit 117 shown in the example of FIG. 1, or one or more other circuits. The variable depolarization sensing threshold can be provided to a depolarization detection circuit, such as an R-wave depolarization detection circuit 106 or a P-wave depolarization detection circuit 116 as shown in the example of FIG. 1, or one or more other detection circuits. The variable depolarization sensing threshold can be indicated by line 330. As illustrated, the variable depolarization sensing threshold can follow a piecewise linear approximation of an exponential decay curve with minimal error between steps. The threshold generation circuit can force the variable depolarization sensing threshold to rapidly follow (e.g. track) the peak level of one or more channels of digital data containing information derived from one or more physiologic sensors (e.g. one or more digitized channels of digital data derived from one or more analog signals representative of cardiac activity such as from an electrocardiogram sensor, or one or more other sensors). When the amplitude of the incoming digital data is greater than the current depolarization sensing threshold, the threshold generation circuit can raise the variable depolarization sensing threshold to a peak threshold value approximately equal to the peak value of the incoming digitized cardiac data as indicated at time T(0). In an example, after a shock or pace pulse is delivered by an implantable medical device, such as a CRM device 100 as shown in the example of FIG. 1 (e.g., a cardioverter/defibrillator, or one or more other devices), the threshold generation circuit can set the variable depolarization sensing threshold to a selected relatively high limit value such as provided by an amplitude-limited portion of the digitized cardiac data or one or more other cardiac signals.

In an embodiment, the threshold generation circuit can decrease the variable depolarization sensing threshold in one or more discrete steps, or in a group of steps comprising multiple discrete steps of a fixed step size. In the embodiment illustrated in FIG. 3, the step group size can be four. Each step group can decrease the variable depolarization sensing threshold by a defined percentage, as indicated by arrows for a four step group between time T(1,0) and T(2,0), arrows for a four step group between T(2,0) and T(3,0), and arrows for a four step group between T(3,0) and T(4,0). The defined percentage for each step group can be preferably approximately 50%. For example, in a preferred embodiment, the value of the variable depolarization sensing threshold at time T(2,0) can be approximately 50% of the value of the variable depolarization sensing threshold at time T(1,0), and the value of the variable depolarization sensing threshold at time T(3,0) can be approximately 50% of the value of the variable depolarization sensing threshold at time T(2,0) or 25% of the value of the variable depolarization sensing threshold at time T(1, 0).

When the variable depolarization sensing threshold decays to a programmable final value, such as specified by a programmable low limit, as indicated at 331, the threshold generation circuit can hold the variable depolarization sensing threshold at the programmable final value until one or more new sensed events occur. The programmable final value can be selected to compensate for noise which is inherent in the sense amplifiers, or other circuits included in the loop (e.g., the final value can be selected to minimize or eliminate spurious sensed events due to noise or the other circuits, or one or more other non-cardiac related events).

In an example, the initial drop percentage can achieve approximately 75% of the peak threshold value, and the four discrete steps in each step group can drop the variable depolarization sensing threshold to approximately 50% of the level of the starting threshold if the four-step group realizes a piecewise geometric progression linear approximation representing an exponential decay curve with minimal error between piecewise steps. Since the depolarization sensing threshold drops in discrete steps as indicated at 332, integer math can be used in the threshold generation circuit. For example in the embodiment of the threshold generation circuit illustrated in FIG. 3, floating point numbers need not be used because the maximum difference/error between any two discrete steps in a four step group is one digital bit (e.g., a factor of 2, or one or more other factors). The present invention can be extended to use any size integer value or number of steps or step groups to achieve the linear approximation of the exponential decay curve. In certain examples, floating point numbers can be optionally used, but can result in increased silicon area needed to implement floating point logic circuits. In an example, implementing the threshold generation circuit in a monolithic integrated circuit where the threshold generation circuit is configured to determine one or more depolarization sensing thresholds at least in part using integer math (e.g. one or more arithmetic operations involving one or more integer values) can result in less power consumption and less silicon area versus using a threshold generation circuit configured to determine the one or more depolarization sensing thresholds using floating point math.

Figure 4:
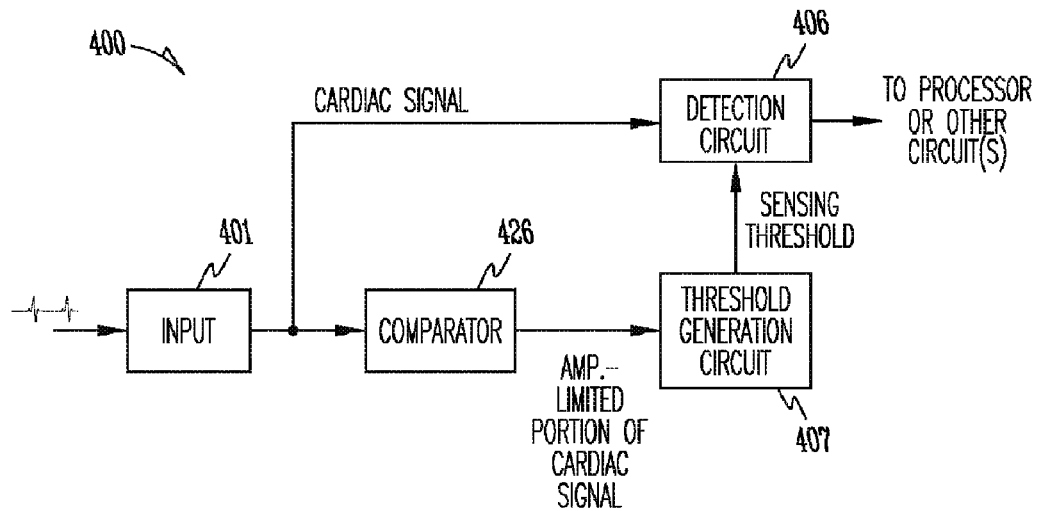
FIG. 4 illustrates generally an example of at least a portion of an implantable medical device.

FIG. 4 illustrates generally an example of at least a portion of an implantable medical device, such as a CRM device 100 as shown in the example of FIG. 1. In the example of FIG. 4, an input 401 can receive a cardiac signal representative of cardiac electrical activity such as one or more intrinsic cardiac events, (e.g., one or more intrinsic depolarizations or evoked responses, or one or more other electrical signals). In an example, the input 401 can include an analog-to-digital converter (A/D), or one or more other circuits to convert an analog signal representative of cardiac electrical activity into a digital signal. In the example of FIG. 4, the input 401 can be coupled to a first comparator 426, and configured to provide the cardiac signal to the comparator 426. In this example, the first comparator 426 can be coupled to a threshold generation circuit 407, and configured to receive the cardiac signal. In this example, the first comparator 426 can be configured to provide an amplitude-limited portion of the cardiac signal to the threshold generation circuit 407. In certain examples, the first comparator can provide the amplitude-limited portion of the cardiac signal using one or more programmable limits (e.g., a programmable peak limit such as a high limit 224 as shown in the example of FIG. 2, or a programmable minimum such as a low limit 225 as shown in the example of FIG. 2, or one or more other limits).

In the example of FIG. 4, the threshold generation circuit can be configured to provide a fixed or variable depolarization sensing threshold, such as a time-varying depolarization sensing threshold, to a detection circuit 406. In an example, the detection circuit can include one or more comparators, such as a second comparator, coupled to the input 401 (such as the input 220 as shown in the example of FIG. 2), and the second comparator can be configured to compare the cardiac signal with the fixed or variable depolarization sensing threshold. In an example, the second comparator can be configured to provide an event signal to another circuit, such as a processor or one or more other circuits, when the cardiac signal exceeds the fixed or variable depolarization sensing threshold.

In certain examples, one or more of the input 401, the first comparator 426, the detection circuit 406, or threshold generation circuit 407 can be a portion, part or component of an integrated circuit, printed circuit assembly, or one or more other circuits, modules, components or portions included in the implantable medical device, such as the CRM device 100 shown in the example of FIG. 1.

In an example, the threshold generation circuit 407 can include one or more peak detectors, the peak detectors coupled to the first comparator 426 can configured to receive the amplitude-limited portion of the cardiac signal. In this example, the one or more peak detectors can be configured to determine a peak or minimum value of the amplitude-limited portion of the cardiac signal, and in response, the threshold generation circuit can be configured to provide the peak or the minimum value as the depolarization sensing threshold to be used by, for example, the detection circuit 406.

Figure 5:
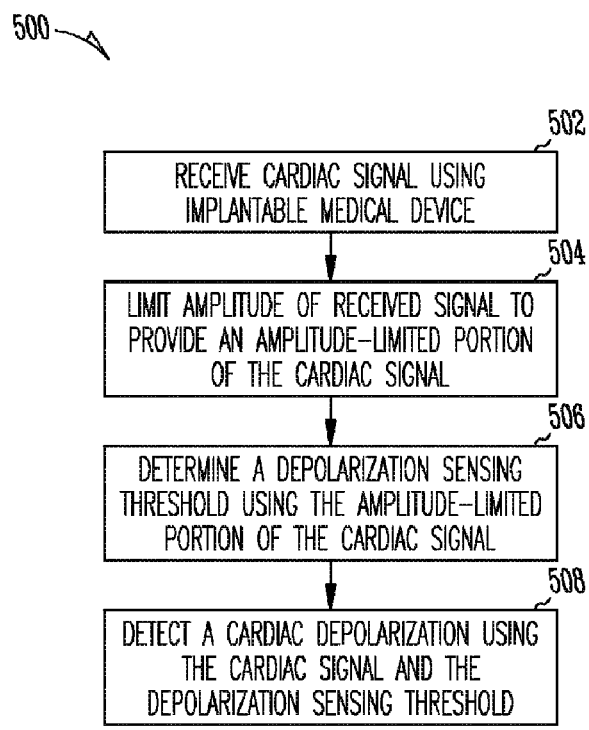
FIG. 5 illustrates generally a portion of a method for automatically determining a depolarization sensing threshold.

FIG. 5 illustrates generally a portion of a method 500 for automatically determining a depolarization sensing threshold that can be used to detect one or more cardiac depolarizations. At 502, a cardiac signal representative of cardiac electrical activity such as one or more cardiac events, (e.g., one or more intrinsic depolarizations or evoked responses, or one or more other electrical signals) can be received, such as by using an input 220, or an input 401 as shown in the examples of FIGS. 2, 4, respectively, or one or more other modules or circuits configured to receive the cardiac signal.

At 504, an amplitude of the received cardiac signal can be limited to provide an amplitude-limited portion of the cardiac signal, such as by using one or more comparators such as a first comparator 426 as shown in the example of FIG. 4, or one or more other circuits or modules. In an example, one or more programmable limits such as a programmable low limit 225, or a programmable high limit 224 such as discussed in FIG. 2, can be used to specify one or more limits (e.g., a peak limit or a minimum) to be used to provide the amplitude-limited portion of the cardiac signal.

At 506, the depolarization sensing threshold can be determined using the amplitude-limited portion of the cardiac signal. In certain examples, the depolarization sensing threshold for a current cardiac cycle can be determined using a peak or minimum value of the amplitude-limited portion of the cardiac signal corresponding to one or more previous depolarizations from one or more previous cardiac cycles. In certain examples, a moving average, weighted average, arithmetic mean, geometric mean, median, other central tendency, or one or more other features of one or more previous depolarizations included in the amplitude-limited portion of the cardiac signal can be used to determine the depolarization sensing threshold for the current cardiac cycle.

At 508, the cardiac signal can include one or more depolarizations, and the one or more depolarizations can be detected using the depolarization sensing threshold determined previously, such as at 506. In certain examples, the detecting the one or more depolarizations can use a detection circuit such as a detection circuit 406 as shown in the example of FIG. 4.

Figure 6:
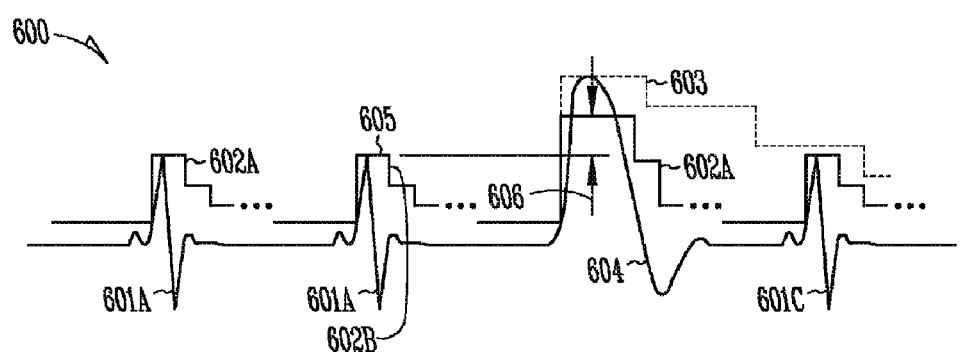
FIG. 6 illustrates generally an illustrative example of cardiac electrical activity over time.

FIG. 6 illustrates generally an illustrative example of cardiac electrical activity over time, such as can be represented by a cardiac signal. A first depolarization 601A can be detected when the first depolarization 601A waveform crosses (e.g., exceeds or equals) a first variable depolarization threshold sequence 602A. One or more variable depolarization threshold sequences can be provided by a threshold generation circuit, such as a threshold generation circuit 407 as shown in the example of FIG. 4, and the sequence of variable depolarization sensing thresholds can follow a pattern or progression such as with respect to time, for example, as shown and discussed in the example of FIG. 3.

A peak of the first variable depolarization threshold sequence 602A can be determined as the peak value of the first depolarization 601A. In some examples, a first peak of the first variable depolarization threshold sequence 602A can be a peak value of an amplitude-limited portion of the cardiac signal as shown in the examples of FIGS. 4-5. During a particular cardiac cycle, such as throughout an interval between the first depolarization 601A and a second depolarization 601B, the depolarization sensing threshold can be adjusted downwards to a final value 331, such as discussed above in the context of FIG. 3. When the second depolarization 601B exceeds the depolarization sensing threshold final value, a second peak 605 of a second depolarization threshold sequence 602B can be determined. In this illustrative example, the first depolarization 601A, and the second depolarization 601B, can have a typical amplitude. A depolarization having an abnormally large amplitude, such as a PVC 604, can result in an elevated peak depolarization sensing threshold 603. In this example, if a variable depolarization sensing threshold can be adjusted or controlled to "track" one or more peak values of one or more previous or current depolarizations, then the peak value of the depolarization sensing threshold can be elevated when a depolarization having abnormally large amplitude occurs, such as the PVC 604. In certain examples, a third peak 606, of a third depolarization sensing threshold sequence can be limited, such as by a programmable percentage or ratio to one or more previous peak values (such as the second peak 605, or one or more other features of one or more previous depolarizations, such as indicated by arrows in FIG. 6). The present inventors have recognized that by limiting a change in the peak of the depolarization sensing threshold sequence (such as the second peak 605 or the third peak 606), under-sensing can be avoided when a depolarization of abnormal amplitude (e.g., a PVC 604) is followed by a depolarization of typical amplitude, such as a third depolarization 601C. For example, if the elevated peak depolarization sensing threshold 603 is used, the typical amplitude of the third depolarization 601C can fail to exceed the elevated peak depolarization sensing threshold 603, as compared to the limited third peak 606. In an example, an absolute value of one or more depolarizations such as the first depolarization 601A, the second depolarization 601B, or the third depolarization 601C can be used to detect one or more depolarizations when compared to one or more depolarization threshold sequences such as the first variable depolarization threshold sequence 601A, or the second variable depolarization threshold sequence 601B, or the third variable depolarization threshold sequence 601C. In this example, the absolute value can be compared with one or more depolarization sensing thresholds, and a depolarization can be detected when the absolute value of the cardiac electrical activity exceeds the one or more depolarization sensing thresholds.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device, comprising:
an input configured to receive a cardiac signal;
a first comparator configured to receive the cardiac signal from the input and to provide an amplitude-limited portion of the cardiac signal, wherein the amplitude-limited portion of the cardiac signal is amplitude-limited by one or more programmable thresholds;
a depolarization sensing threshold generation circuit configured to provide a depolarization sensing threshold using the amplitude-limited portion of the cardiac signal, wherein the amplitude-limited portion of the cardiac signal provided to the depolarization sensing threshold generation circuit excludes one or more portions of the cardiac signal; and
a depolarization detection circuit configured to detect a cardiac depolarization using the cardiac signal and the depolarization sensing threshold.

2. The implantable medical device of claim 1, wherein the input includes an analog-to-digital (A/D) converter configured to convert an analog signal representative of cardiac activity into digital data; and
wherein the cardiac signal includes the digital data.

3. The implantable medical device of claim 2, wherein the depolarization sensing threshold generation circuit is configured to provide the depolarization sensing threshold at least in part using integer math.

4. The implantable medical device of claim 2, wherein the A/D converter is configured to convert the analog signal into digital data using a single gain range without requiring clipping of the analog signal when the analog signal includes both a depolarization of a typical amplitude and a depolarization of amplitude substantially greater than the depolarization of the typical amplitude.

5. The implantable medical device of claim 1, wherein the depolarization sensing threshold generation circuit includes a peak detector configured to receive the amplitude-limited portion of the cardiac signal, to detect at least one of a peak or a minimum of the amplitude-limited portion of the cardiac signal, and to provide at least one of the detected peak or the detected minimum of the amplitude-limited portion of the cardiac signal to the depolarization sensing threshold generation circuit; and wherein the depolarization sensing threshold is substantially equal to at least one of the detected peak or the detected minimum of the amplitude-limited portion of the cardiac signal.

6. The implantable medical device of claim 1, wherein the depolarization detection circuit includes a second comparator configured to compare the cardiac signal with the depolarization sensing threshold and to provide an event signal when the cardiac signal exceeds the depolarization sensing threshold.

7. The implantable medical device of claim 6, wherein the depolarization sensing threshold generation circuit is configured to provide the depolarization sensing threshold to the detection circuit for a current cardiac cycle in response to the event signal.

8. The implantable medical device of claim 7, wherein the depolarization sensing threshold generation circuit is configured to vary the depolarization sensing threshold level as a function of time during a particular cardiac cycle.

9. The implantable medical device of claim 8, wherein the depolarization threshold generation circuit is configured to determine a depolarization sensing threshold peak value for a current cardiac cycle using a depolarization sensing threshold peak value from a previous cardiac cycle and the amplitude-limited portion of the cardiac signal.

10. The implantable medical device of claim 9, wherein the depolarization sensing threshold generation circuit is configured to decrease the depolarization sensing threshold as a function of time, during the particular cardiac cycle, in one or more discrete steps following a piecewise linear approximation of a geometric progression; and wherein the one or more discrete steps includes a first depolarization sensing threshold provided at the beginning of the particular cardiac cycle, and a second depolarization sensing threshold equal to approximately 75% of the first depolarization sensing threshold.

11. The implantable medical device of claim 1, wherein the amplitude-limited portion of the cardiac signal is produced by the first comparator limiting the amplitude of the received cardiac signal using at least one programmable limit.

12. A method, comprising:
receiving a cardiac signal using an implantable medical device;
limiting an amplitude of the received cardiac signal to provide an amplitude-limited portion of the cardiac signal, wherein the amplitude-limited portion of the cardiac signal is amplitude-limited by one or more programmable thresholds;
determining a depolarization sensing threshold using the amplitude-limited portion of the cardiac signal, wherein the amplitude-limited portion of the cardiac signal used to determine the depolarization sensing threshold excludes one or more portions of the cardiac signal; and
detecting a cardiac depolarization using the cardiac signal and the depolarization sensing threshold.

13. The method of claim 12, including detecting a peak of a received cardiac signal during a particular cardiac cycle; and
wherein the limiting the amplitude includes limiting the amplitude of the received cardiac signal to a percentage relative to the peak, the percentage specified using at least one programmable limit, to provide the amplitude-limited portion of the cardiac signal.

14. The method of claim 12, wherein the determining the depolarization sensing threshold includes:
detecting at least one of a peak or a minimum of the amplitude-limited portion of the cardiac signal; and
providing, in response to the detecting, a depolarization sensing threshold substantially equal to at least one of the detected peak or the detected minimum of the amplitude-limited portion of the cardiac signal.

15. The method of claim 12, wherein the detecting the cardiac depolarization includes:
comparing the received cardiac signal with the depolarization sensing threshold; and
providing an event signal when the received cardiac signal exceeds the depolarization sensing threshold.

16. The method of claim 15, wherein the determining the depolarization sensing threshold includes providing a depolarization sensing threshold substantially equal to at least one of the peak or the minimum of the amplitude-limited portion of the cardiac signal in response to the event signal.

17. The method of claim 12, wherein the determining the depolarization sensing threshold includes varying the depolarization sensing threshold as a function of time during a particular cardiac cycle.

18. The method of claim 17, wherein the determining the depolarization sensing threshold includes determining a depolarization sensing threshold peak for a current cardiac cycle using a depolarization sensing threshold peak value from a previous cardiac cycle and the amplitude-limited portion of the cardiac signal.

19. The method of claim 17, wherein the determining the depolarization sensing threshold includes decreasing the depolarization sensing threshold in one or more discrete steps following a piecewise linear approximation of a geometric progression; and
wherein the one or more discrete steps includes using a first depolarization sensing threshold, provided at the beginning of the particular cardiac cycle, and using a second. depolarization sensing threshold equal to approximately 75% of the first depolarization sensing threshold at a later time during the particular cardiac cycle.

20. The method of claim 12, wherein the receiving the signal includes:
receiving an analog signal representative of the cardiac activity; and
converting the analog signal into a digital signal using an analog-to-digital (A/D) converter.

21. The method of claim 12, wherein the receiving the signal includes:
receiving an analog signal representative of the cardiac activity; and
converting the analog signal into a digital signal using an analog-to-digital (A/D) converter having a single gain range without requiring clipping of the analog signal when the analog signal comprises both a depolarization of a typical amplitude and a depolarization of amplitude substantially greater than the depolarization of the typical amplitude.

* * * * *